United States Patent
Paschall, Jr.

[11] Patent Number: 6,074,344
[45] Date of Patent: Jun. 13, 2000

[54] GRASPING RETRACTOR

[76] Inventor: Jack Paschall, Jr., 209 E. Bay Front, Newport Beach, Calif. 92662

[21] Appl. No.: 09/353,105

[22] Filed: Jul. 14, 1999

[51] Int. Cl.[7] .................................................. A61B 17/02
[52] U.S. Cl. .......................................... 600/218; 600/210
[58] Field of Search ................................... 600/210, 218, 600/216, 217, 214, 219

[56]  References Cited

U.S. PATENT DOCUMENTS

| | | |
|---|---|---|
| 569,839 | 10/1896 | Roeloffs . |
| 1,060,738 | 5/1913 | Binney ..................................... 600/218 |
| 2,702,540 | 2/1955 | Debeh . |
| 3,394,700 | 7/1968 | Yamamoto . |
| 3,651,800 | 3/1972 | Willbanks ............................... 600/210 |
| 3,729,006 | 4/1973 | Wilder et al. ........................... 600/210 |
| 3,752,152 | 8/1973 | Kern . |
| 4,034,746 | 7/1977 | Williams . |
| 4,051,844 | 10/1977 | Chiulli ..................................... 600/217 |
| 5,052,374 | 10/1991 | Alvarez-Jacinto . |
| 5,474,057 | 12/1995 | Makower et al. . |
| 5,520,610 | 5/1996 | Giglio et al. . |
| 5,529,571 | 6/1996 | Daniel . |

FOREIGN PATENT DOCUMENTS

| | | | |
|---|---|---|---|
| 995535 | 8/1976 | Canada .................................. 600/210 |

*Primary Examiner*—Paul J. Hirsch

[57] ABSTRACT

The grasping retractor has an arm member and a blade member with a jaw portion at one end and a recurved handle portion at the other end. A clamping bracket is pivotally attached to the blade member, and has a jaw portion located to move into engagement with the jaw portion of the blade member when the clamping bracket is pivoted. A locking mechanism holds the clamping bracket secure, allowing the blade member to function as a retractor without slipping.

11 Claims, 2 Drawing Sheets

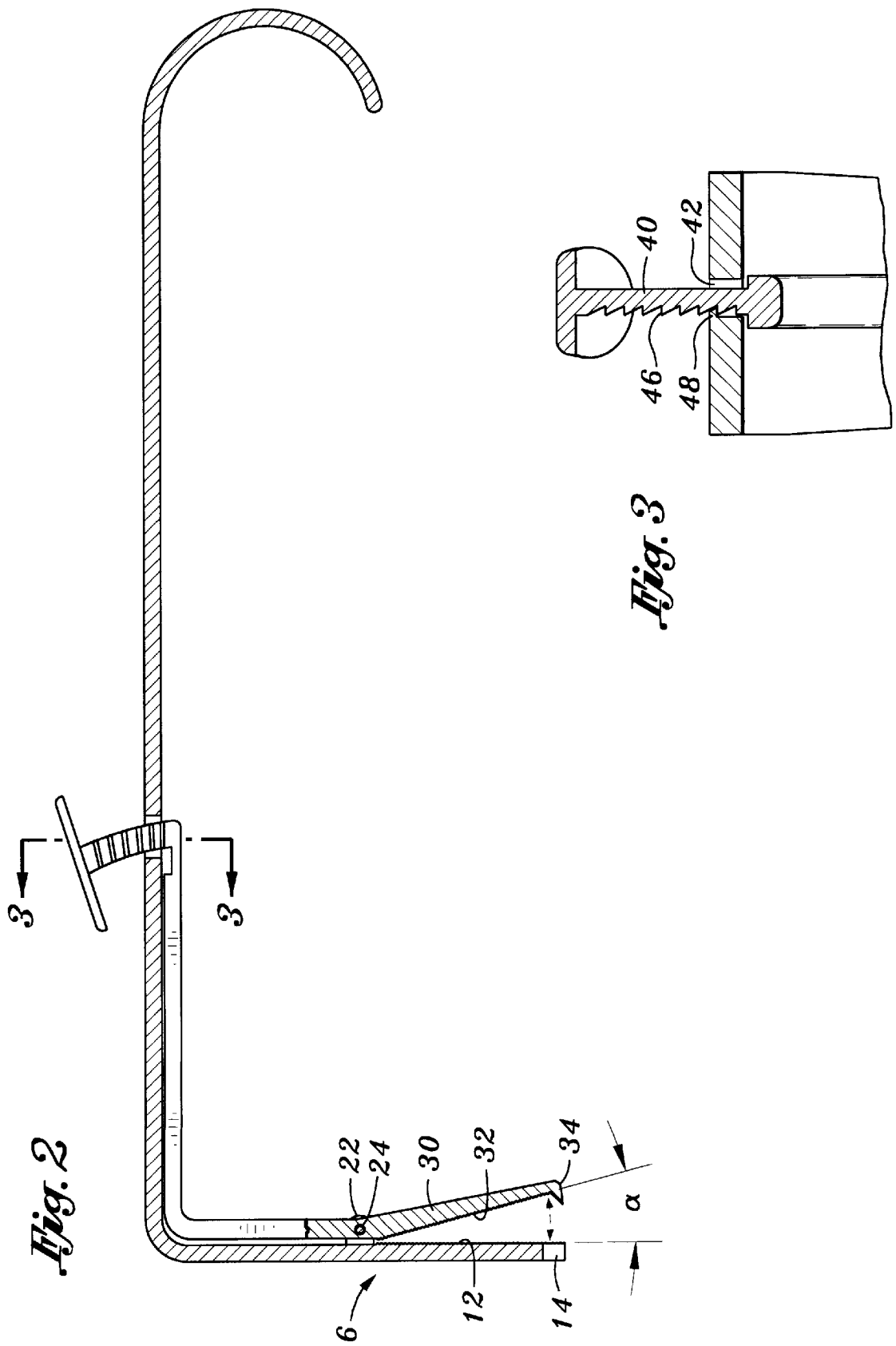

GRASPING RETRACTOR

SUMMARY OF THE INVENTION

The preferred grasping retractor includes an arm member with a handle at one end and a blade at the other end. Preferably the blade is turned to be at an angle, such as a right angle, to the major axis of the arm member, and has at its outer end a jaw portion. A clamping bracket is pivotally attached to the blade member, and is shaped to generally follow the shape of the arm member and the blade member. The clamping bracket includes a jaw portion that lies adjacent the jaw portion of the blade member, such that when the clamping bracket pivots the jaw portions of the clamping bracket and blade member move toward one another to clamp tissue between them. Preferably the retractor includes structure to selectively hold the blade member and clamping bracket in any of various given pivotal positions, such that upon clamping a selected tissue the blade member may be manually manipulated to move and control the tissue behind the blade as desired.

BRIEF DESCRIPTION OF THE DRAWING

The invention will be further described in connection with the accompanying drawing in which:

FIG. 2 is an enlarged, partial cross-sectional view taken on lines II—II of FIG. 1; and FIG. 3 is an enlarged, partial cross-sectional view taken on lines III—III of FIG. 1.

DETAILED DESCRIPTION

Figure 1:
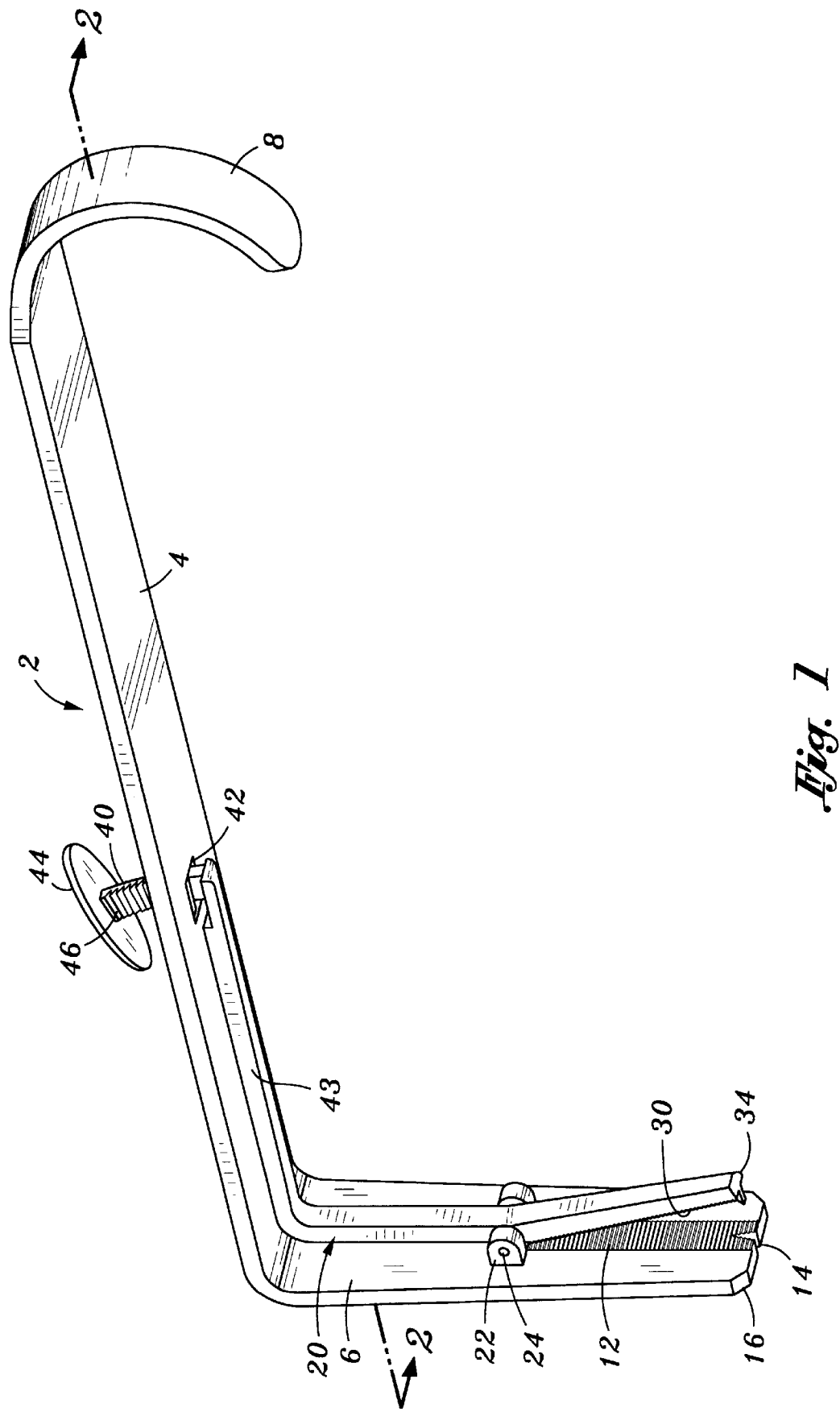
FIG. 1 is a perspective view of a clamping retractor constructed in accordance with the present invention.

The present invention concerns a grasping retractor of simple construction that can be manipulated to seize and hold a selected tissue, especially an internal tissue, permitting the surgeon or an assistant to manipulate the held tissue as desired. It proceeds from the recognition that complex structures are often more difficult and troublesome, and require greater attention, than simple structures. In the often challenging environment of a surgical procedure, where attention must be focused on the patient and the procedure, having to stop and give attention to applying or adjusting a complex instrumentation is not desirable. Yet while simple, easily used surgical devices are desirable, many of those developed in recent years and decades are anything but simple.

The present invention provides a grasping retractor of simple construction, one that is easily used, does not require much attention yet is quite effective, and one which because of its simplicity and effectiveness could be adaptable to one-time, disposable use.

A presently preferred construction of the retractor is shown in perspective in FIG. 1. The retractor 2 has an arm member 4 which, at one end terminates in a blade portion 6, and at the other end a recurved handle portion 8. Preferably the blade portion is turned approximately 90 degrees, as shown, to be at a right angle to the major axis of the arm member. Also preferably the blade portion 6 includes serrations 12 and a notch 14. A chamfer 16 at each end corner of the blade portion narrows and rounds its tip.

A clamping bracket 20, shaped to lie generally adjacent the arm member 4 and the blade portion 6, is pivotally attached to the blade portion 6. As shown more specifically in FIG. 2, the blade portion includes a boss or clip 22 with upstanding tabs that lie alongside the clamping bracket. A pivot pin 24 passes through the tabs of the clip 22 and through the portion of the bracket received in the clip 22, thereby pivotally attaching the clamping bracket to the blade portion. The range of motion of the clamping bracket relative to the blade portion is such that a jaw portion 30 at one end of the clamping bracket may be moved either into engagement with the jaw portion 30 of the blade portion 6, or to a position in which the outer ends of the jaw portion 30 are well spaced from one another as shown in FIG. 1.

The jaw portion 30 of the clamping bracket has, at one end, internal serrations 32 that, when the jaw portion 30 of the clamping bracket and blade portion 6 are in contact, mesh or interfit with the serrations 12 on blade portion 6. Also, jaw portion 30 has, at its outer end, a tooth 34 shaped and located to fit into notch 14, thereby to assist in holding tissue to which the grasping retractor has been applied.

The clamping bracket includes, at its other end, an arcuate shaft 40 that is received in and extends through an opening 42 in the arm member, as shown in FIG. 3. Preferably the shaft is an extension of the arm portion 43 of the clamping bracket that underlies the arm member as shown. Arm portion 43 is about as long as the portion terminating in jaw portion 30. The arc of the shaft is such that, when the clamping bracket pivots around pivot pin 24, the shaft clears the sides of the opening and moves easily relative to the arm member. A pad 44 is provided at the outer end of the shaft to assist in manually moving the shaft through the opening to pivot the jaw portions and clamp or release tissue. Teeth 46 on the side of the shaft interfit with a detent 48 provided on one side of opening 42, thereby to permit the user to selectively fix or lock the angular position of the clamping member relative to the arm member. The clamping is easily disengaged by pushing the shaft 40 away from the detent 48.

In use during a surgical procedure, one or more of the grasping retractors may be attached to any of various anatomical structures by grasping the selected tissue between the jaw portions and the moving shaft 40 to engage one of the teeth 46 with detent 48. Then, at any desired time, and for however long as desired, the selected tissue may be moved easily and quickly in whatever direction might be desired simply by grasping handle portion 8, repositioning it, and holding it in that position. Usually the surgeon will instruct an assistant to do this.

The grasping retractor is particularly useful and effective in manipulating internal tissues and structures. For example, if fascia or joint capsule must be held aside during a surgical procedure, the surgeon simply attaches appropriately the grasping retractor then instructs an assistant to hold the handle of the retractor in an appropriate orientation for as long as necessary. Because the arm portion 43 of the clamping bracket is about as long as the jaw portion 30, the arcuate shaft and its pad are convenient to the surgeon, whose attention is focused on the structure being grasped, and are readily actuated to close and lock the jaw portions to the desired structure. If the surgeon positions the retractor the assistant may not need to see what is being grasped and held back by the blade portion 6. The assistant may release his hold on the arm member 4 and the retractor will remain in a safe position, because of the attachment to the desired tissue by the grasping mechanism. The retractor remains in position by virtue of the jaw position, thus avoiding repeated application because of slipping, as is necessary using ordinary right angle retractors. This feature avoids possible tissue damage repeated application may produce.

While the grasping retractor may be made in various sizes, in one preferred construction both the arm member and the clamping bracket were made from a surgical grade stainless steel about 1/16 of an inch thick. The main portion of the arm member was 1 inch wide, and of an overall length of about 9½ inches. The angled blade portion of the arm member was about 3 inches long. Each chamfer at the tip of the arm's blade was about 3/8 inch by 3/8 inch. The notch in the blade, and the tooth at the tip of the bracket's blade, were each about 1/8 inch wide and 1/4 inch long. The handle portion of the arm member was reduced in width to about ½ inch, each side being narrowed about 1/4 of an inch. The reduction began about 1 inch from the outer surface of the handle's arc, looking down on the handle from above. The angle of the clamping bracket, and the range of movement permitted by the length of the arched shaft, was such that the jaws swung apart about 1/4 inch. Of course, others might prefer different overall sizes and dimensional relationships of the various elements of the grasping retractor. It is well within the skill of those experienced in designing such instruments to make such modifications.

The opening 42 in the arm member 4 for passage of the clamping bracket is designed to allow the entire clamping bracket to be passed through the opening during assembly of the retractor during manufacture. Thus the retractor can be made of just two parts.

While a preferred embodiment of the invention has been shown and described, because modifications will be apparent to those of ordinary skill in this field, the scope of the invention is not limited to the disclosed construction but rather is as set forth in the following claims.

What is claimed is:

1. A grasping retractor for use in surgical procedures, the retractor including:

an elongated arm member having a major axis and two end segments, one end segment being a handle, the other end segment being a blade, the blade terminating in a jaw portion, the blade being at an angle to the major axis of the arm member, a clamping bracket having two end segments, one end segment being a jaw portion, and means pivotally attaching the clamping bracket to the blade member such that the jaw portions of the blade member and clamping bracket may be selectively moved towards and away from one another to selectively grasp and hold tissue between the cooperating jaw portions.

2. A grasping retractor as set forth in claim 1 in which the jaw portions of the blade member and the clamping bracket include cooperating serrations to assist in holding tissue between the cooperating jaw portions.

3. A grasping retractor as set forth in claim 1 further including:

a locking mechanism to hold the jaw portions of the blade member and clamping bracket in any of a multiplicity of angular relationships, thereby to grasp and hold tissue of any of various thicknesses between the jaw portions.

4. A grasping retractor as set forth in claim 3 in which the blade of the arm member is at an angle of approximately ninety degrees to the main axis of the arm member.

5. A grasping retractor as set forth in claim 4 in which the jaw portions of the blade member and the clamping bracket include cooperating serrations to assist in holding tissue between the cooperating jaw portions.

6. A grasping retractor as set forth in claim 5 in which one jaw portion includes a tooth extending toward the other jaw portion, and in which the other jaw portion includes a notch shaped and located to receive the tooth when the jaw portions are moved into engagement with one another.

7. A grasping retractor as set forth in claim 1 in which the means pivotally attaching the clamping bracket to the blade member includes a first component on the arm member and a second component on the clamping bracket, the first and second components being adjacent one another, and a pivot pin extending through the first and second components to pivotally attach the clamping bracket to the blade member.

8. A grasping retractor as set forth in claim 3 in which the means pivotally attaching the clamping bracket to the blade member includes a first component on the blade member and a second component on the clamping bracket, the first and second components being adjacent one another, and a pivot pin extending through the first and second components to pivotally attach the clamping bracket to the blade member.

9. A grasping retractor as set forth in claim 8 in which the blade of the arm member is at an angle of approximately ninety degrees to the main axis of the arm member, and in which the jaw portions of the blade member and the clamping bracket include cooperating serrations to assist in holding tissue between the cooperating jaw portions, and in which one jaw portion includes a tooth extending toward the other jaw portion, the other jaw portion including a notch shaped and located to receive the tooth when the jaw portions are moved into engagement with one another.

10. A grasping retractor as set forth in claim 9 in which the components are of surgical stainless steel.

11. A grasping retractor as set forth in claim 9 in which the components are made of a material suitable for a one time, disposable use.

\* \* \* \* \*

UNITED STATES PATENT AND TRADEMARK OFFICE
CERTIFICATE OF CORRECTION

PATENT NO.     : 6,074,344
DATED          : June 13, 2000
INVENTOR(S)    : Jack Paschall, Jr.

It is certified that error appears in the above-identified patent and that said Letters Patent is hereby corrected as shown below:

<u>Columns 1 - 4,</u>
Should be deleted, and substitute therefor columns 1 - 4, as shown on the attached pages.

Signed and Sealed this

Nineteenth Day of November, 2002

Attest:

Attesting Officer

JAMES E. ROGAN
Director of the United States Patent and Trademark Office

GRASPING RETRACTOR

This invention relates to a retractor for use in surgical procedures, especially a retractor adapted to selectively grasp and hold internal tissues.

The medical profession has long used retractors in surgical procedures. Many different designs exist. Some designs are intended for particular tissues or surgical procedures; some are intended to hold open the edges of a surgical incision; some are intended to lift or hold internal tissues. An example of the latter type of retractor is presented in Giglio et al. U.S. Pat. No. 5,520,610 issued May 28, 1996. As is typical of many of the more recent retractor designs, the Giglio retractor is a complex structure with components for holding open a surgical incision, and components for lifting and holding internal structures such as a length of intestine. Another example of such an internal and external tissue retractor is presented in Alvarez-Jacinto U.S. Pat. No. 5,052,374 issued Oct. 1, 1991.

Obviously, a retractor designed to hold most any type of tissue is of greater usefulness than a retractor limited to a particular tissue or procedure. Also, a simple retractor, with few components and an open, exposed design, one easily cleaned and sterilized, has more appeal than a structurally complex, difficult to clean and sterilize retractor construction.

An object of the present invention is to provide a retractor for any of various surgical procedures that has a simple construction, that is easily cleaned and sterilized, and that is relatively inexpensive to manufacture and adaptable to a one time, disposable use. These and other objects of the invention will be apparent to those in this field from the following description of a preferred construction.

SUMMARY OF THE INVENTION

The preferred grasping retractor includes an arm member with a handle at one end and a blade at the other end. Preferably the blade is turned to be at an angle, such as a right angle, to the major axis of the arm member, and has at its outer end a jaw portion. A clamping bracket is pivotally attached to the blade member, and is shaped to generally follow the shape of the arm member and the blade member. The clamping bracket includes a jaw portion that lies adjacent the jaw portion of the blade member, such that when the clamping bracket pivots the jaw portions of the clamping bracket and blade member move toward one another to clamp tissue between them. Preferably the retractor includes structure to selectively hold the blade member and clamping bracket in any of various given pivotal positions, such that upon clamping a selected tissue the blade member may be manually manipulated to move and control the tissue behind the blade as desired.

BRIEF DESCRIPTION OF THE DRAWING

The invention will be further described in connection with the accompanying drawing in which:

FIG. 1 is a perspective view of a clamping retractor constructed in accordance with the present invention;

FIG. 2 is an enlarged, partial cross-sectional view taken on lines II—II of FIG. 1; and FIG. 3 is an enlarged, partial cross-sectional view taken on lines III—III of FIG. 1.

DETAILED DESCRIPTION

The present invention concerns a grasping retractor of simple construction that can be manipulated to seize and hold a selected tissue, especially an internal tissue, permitting the surgeon or an assistant to manipulate the held tissue as desired. It proceeds from the recognition that complex structures are often more difficult and troublesome, and require greater attention, than simple structures. In the often challenging environment of a surgical procedure, where attention must be focused on the patient and the procedure, having to stop and give attention to applying or adjusting a complex instrumentation is not desirable. Yet while simple, easily used surgical devices are desirable, many of those developed in recent years and decades are anything but simple.

The present invention provides a grasping retractor of simple construction, one that is easily used, does not require much attention yet is quite effective, and one which because of its simplicity and effectiveness could be adaptable to one-time, disposable use.

A presently preferred construction of the retractor is shown in perspective in FIG. 1. The retractor 2 has an arm member 4 which, at one end terminates in a blade portion 6, and at the other end a recurved handle portion 8. Preferably the blade portion is turned approximately 90 degrees, as shown, to be at a right angle to the major axis of the arm member. Also preferably the blade portion 6 includes serrations 12 and a notch 14. A chamfer 16 at each end corner of the blade portion narrows and rounds its tip.

A clamping bracket 20, shaped to lie generally adjacent the arm member 4 and the blade portion 6, is pivotally attached to the blade portion 6. As shown more specifically in FIG. 2, the blade portion includes a boss or clip 22 with upstanding tabs that lie alongside the clamping bracket. A pivot pin 24 passes through the tabs of the clip 22 and through the portion of the bracket received in the clip 22, thereby pivotally attaching the clamping bracket to the blade portion. The range of motion of the clamping bracket relative to the blade portion is such that a jaw portion 30 at one end of the clamping bracket may be moved either into engagement with the jaw portion 30 of the blade portion 6, or to a position in which the outer ends of the jaw portion 30 are well spaced from one another as shown in FIG. 1.

The jaw portion 30 of the clamping bracket has, at one end, internal serrations 32 that, when the jaw portion 30 of the clamping bracket and blade portion 6 are in contact, mesh or interfit with the serrations 12 on blade portion 6. Also, jaw portion 30 has, at its outer end, a tooth 34 shaped and located to fit into notch 14, thereby to assist in holding tissue to which the grasping retractor has been applied.

The clamping bracket includes, at its other end, an arcuate shaft 40 that is received in and extends through an opening 42 in the arm member, as shown in FIG. 3. Preferably the shaft is an extension of the arm portion 43 of the clamping bracket that underlies the arm member as shown. Arm portion 43 is about as long as the portion terminating in jaw portion 30. The arc of the shaft is such that, when the clamping bracket pivots around pivot pin 24, the shaft clears the sides of the opening and moves easily relative to the arm member. A pad 44 is provided at the outer end of the shaft to assist in manually moving the shaft through the opening to pivot the jaw portions and clamp or release tissue. Teeth 46 on the side of the shaft interfit with a detent 48 provided on one side of opening 42, thereby to permit the user to selectively fix or lock the angular position of the clamping member relative to the arm member. The clamping is easily disengaged by pushing the shaft 40 away from the detent 48.

In use during a surgical procedure, one or more of the grasping retractors may be attached to any of various anatomical structures by grasping the selected tissue between the jaw portions and the moving shaft 40 to engage one of the teeth 46 with detent 48. Then, at any desired time, and for however long as desired, the selected tissue may be moved easily and quickly in whatever direction might be desired simply by grasping handle portion 8, repositioning it, and holding it in that position. Usually the surgeon will instruct an assistant to do this.

The grasping retractor is particularly useful and effective in manipulating internal tissues and structures. For example, if fascia or joint capsule must be held aside during a surgical procedure, the surgeon simply attaches appropriately the grasping retractor then instructs an assistant to hold the handle of the retractor in an appropriate orientation for as long as necessary. Because the arm portion 43 of the clamping bracket is about as long as the jaw portion 30, the arcuate shaft and its pad are convenient to the surgeon, whose attention is focused on the structure being grasped, and are readily actuated to close and lock the jaw portions to the desired structure. If the surgeon positions the retractor the assistant may not need to see what is being grasped and held back by the blade portion 6. The assistant may release his hold on the arm member 4 and the retractor will remain in a safe position, because of the attachment to the desired tissue by the grasping mechanism. The retractor remains in position by virtue of the jaw position, thus avoiding repeated application because of slipping, as is necessary using ordinary right angle retractors. This feature avoids possible tissue damage repeated application may produce.

While the grasping retractor may be made in various sizes, in one preferred construction both the arm member and the clamping bracket were made from a surgical grade stainless steel about 1/16 of an inch thick. The main portion of the arm member was 1 inch wide, and of an overall length of about 9½ inches. The angled blade portion of the arm member was about 3 inches long. Each chamfer at the tip of the arm's blade was about ⅜ inch by ⅜ inch. The notch in the blade, and the tooth at the tip of the bracket's blade, were each about ⅛ inch wide and ¼ inch long. The handle portion of the arm member was reduced in width to about ½ inch, each side being narrowed about ¼ of an inch. The reduction began about 1 inch from the outer surface of the handle's arc, looking down on the handle from above. The angle of the clamping bracket, and the range of movement permitted by the length of the arched shaft, was such that the jaws swung apart about ¼ inch. Of course, others might prefer different overall sizes and dimensional relationships of the various elements of the grasping retractor. It is well within the skill of those experienced in designing such instruments to make such modifications.

The opening 42 in the arm member 4 for passage of the clamping bracket is designed to allow the entire clamping bracket to be passed through the opening during assembly of the retractor during manufacture. Thus the retractor can be made of just two parts.

While a preferred embodiment of the invention has been shown and described, because modifications will be apparent to those of ordinary skill in this field, the scope of the invention is not limited to the disclosed construction but rather is as set forth in the following claims.

What is claimed is:

1. A grasping retractor for use in surgical procedures, the retractor including:

an elongated arm member having a major axis and two end segments, one end segment being a handle, the other end segment being a blade, the blade terminating in a jaw portion, the blade being at an angle to the major axis of the arm member, a clamping bracket having two end segments, one end segment being a jaw portion, and means pivotally attaching the clamping bracket to the blade member such that the jaw portions of the blade member and clamping bracket may be selectively moved towards and away from one another to selectively grasp and hold tissue between the cooperating jaw portions.

2. A grasping retractor as set forth in claim 1 in which the jaw portions of the blade member and the clamping bracket include cooperating serrations to assist in holding tissue between the cooperating jaw portions.

3. A grasping retractor as set forth in claim 1 further including:

a locking mechanism to hold the jaw portions of the blade member and clamping bracket in any of a multiplicity of angular relationships, thereby to grasp and hold tissue of any of various thicknesses between the jaw portions.

4. A grasping retractor as set forth in claim 3 in which the blade of the arm member is at an angle of approximately ninety degrees to the main axis of the arm member.

5. A grasping retractor as set forth in claim 4 in which the jaw portions of the blade member and the clamping bracket include cooperating serrations to assist in holding tissue between the cooperating jaw portions.

6. A grasping retractor as set forth in claim 5 in which one jaw portion includes a tooth extending toward the other jaw portion, and in which the other jaw portion includes a notch shaped and located to receive the tooth when the jaw portions are moved into engagement with one another.

7. A grasping retractor as set forth in claim 1 in which the means pivotally attaching the clamping bracket to the blade member includes a first component on the arm member and a second component on the clamping bracket, the first and second components being adjacent one another, and a pivot pin extending through the first and second components to pivotally attach the clamping bracket to the blade member.

8. A grasping retractor as set forth in claim 3 in which the means pivotally attaching the clamping bracket to the blade member includes a first component on the blade member and a second component on the clamping bracket, the first and second components being adjacent one another, and a pivot pin extending through the first and second components to pivotally attach the clamping bracket to the blade member.

9. A grasping retractor as set forth in claim 8 in which the blade of the arm member is at an angle of approximately ninety degrees to the main axis of the arm member, and in which the jaw portions of the blade member and the clamping bracket include cooperating serrations to assist in holding tissue between the cooperating jaw portions, and in which one jaw portion includes a tooth extending toward the other jaw portion, the other jaw portion including a notch shaped and located to receive the tooth when the jaw portions are moved into engagement with one another.

10. A grasping retractor as set forth in claim 9 in which the components are of surgical stainless steel.

11. A grasping retractor as set forth in claim 9 in which the components are made of a material suitable for a one time, disposable use.

* * * * *